United States Patent [19]

Letsinger

[11] Patent Number: 5,416,203
[45] Date of Patent: * May 16, 1995

[54] STEROID MODIFIED OLIGONUCLEOTIDES

[75] Inventor: Robert L. Letsinger, Wilmetter, Ill.

[73] Assignee: Northwestern University, Evanston, Ill.

[ * ] Notice: The portion of the term of this patent subsequent to Sep. 18, 2007 has been disclaimed.

[21] Appl. No.: 97,320

[22] Filed: Jul. 26, 1993

Related U.S. Application Data

[63] Continuation of Ser. No. 646,645, filed as PCT/US90/003204 on Jun. 6, 1990.

[51] Int. Cl.$^6$ .............................. C07H 21/00
[52] U.S. Cl. ................... 536/25.34; 536/5; 536/25.31; 536/25.33
[58] Field of Search ............ 536/5, 24.5, 25.1, 26.22, 536/25.31, 25.33, 25.34

[56] References Cited

U.S. PATENT DOCUMENTS 4,958,013  9/1990  Letsinger .................... 536/24.5

OTHER PUBLICATIONS

Letsinger et al., Proc. Natl. Acad. Sci, USA, vol. 86, pp. 6553–6556, Sep. 1989.

Primary Examiner—Douglas W. Robinson
Assistant Examiner—J. Oliver Wilson
Attorney, Agent, or Firm—Reising, Ethington, Barnard, Perry & Milton

[57] ABSTRACT

An oligonucleotide conjugated to a steroid the oligonucleotide comprising:

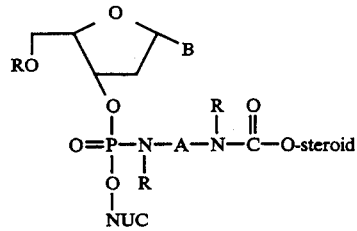

wherein A is selected from the group consisting of an aliphatic alkyl, branched aliphatic alkyl and an alkyl (branched) chain of 2 to 18 carbon atoms, R is selected from the group consisting of H and lower alkyl up to 12 carbon atoms; B is a naturally occurring base, the steroid is bound to the oligonucleotide utilizing the naturally occurring bases through an (-oxycarbonyl-amino)-decylamine-moiety, and NUC is an oligonucleotide.

6 Claims, No Drawings

STEROID MODIFIED OLIGONUCLEOTIDES

This a continuation of application Ser. No. 7/646,645 filed as PCT/US90/003204 on Jun. 6, 1990 now abandoned.

GRANT REFERENCE

This invention was developed with support provided by the National Cooperative Drug Discovery Group for the Treatment of AIDS, Grant U01 A124846 from the National Cancer Institute of Allergy and Infectious Disease and by Grant 5R37GM10265 from the National Institute of General Medical Science.

FIELD OF INVENTION, BACKGROUND AND PRIOR ART

This invention relates to oligonucleotides modified by a pendant steroid group. More particularly, the present invention is related to steroid modified oligonucleotides and a method of using the modified oligonucleotides as antiviral agents.

The pioneering work of Zamecnik and Stephenson, *Proc. Natl. Acad.*, 75:280–284 (1978), on antiviral activity of oligonucleotides and Miller and Ts'o, on the chemistry and biochemistry of non-ionic analogues (Barrett, et al., *Biochem.*, 13:4898–5 (1974) and Jayaraman, et al. *Proc. Natl. Acad. Sci. USA*, 78:1537–1541 (1981)) has stimulated extensive research directed at the therapeutic potential of nucleotide polymers. Oligonucleotide analogues with methylphosphonate, Miller, et al., *Biochemie*, 67:769–776 (1985), Agris, et al., *Biochem.*, 25:6268–6275 (1986), Smith et al., *Proc. Natl. Acad. Sci. USA*, 83:2787–2791 (1986), and Sarin, et al., *Proc. Natl. Acad. Sci. USA*, 85:7448–7451 (1988); phosphorothioate, Matsukura, et al., *Proc. Natl. Acad. Sci. USA*, 85:7079–7083 (1988); and phosphoramidate, Agrawal, et al., *Proc. Natl. Acad. Sci. USA*, 85:7079–7083 (1988), backbones as well as natural type oligonucleotides, Zamecnik, et al., *Proc. Natl. Acad. Sci. USA*, 82:4143–4146 (1986), and a polylysine conjugate, Goodchild, et al., *Proc. Natl. Acad. Sci. USA*, 85:5507–5511 (1988), have now been reported to inhibit viral replication in cell culture. The viruses studied in this context include Rous sarcoma virus, Samecnik and Stephenson, *Proc. Natl. Acad.*, 75:280–284 (1978); simian virus, Miller, et al., *Biochemie*, 67:769–776 (1985); vesticular stomatitis virus, Agris, et al., Biochem., 25:6268–6275 (9186) and Lemaitre, et al., *Proc. Natl. Acad. Sci. USA*, 84:648–652 (1987); human immunodeficiency virus (HIV), Sarin, et al., *Proc. Natl. Acad. Sci. USA*, 85:7448–7451 (1988), Matsukura, et al., *Proc. Natl. Acad. Sci. USA*, 84:7706–7710 (1987), Agrawal, et al., *Proc. Natl. Acad. Sci. USA*, 85:7079–7083 (1988), Aamecnik, et al., *Proc. Natl. Acad. Sci. USA*, 83:4143–4146 (1986), and Goodchild, et al., *Proc. Natl. Acad. Sci. USA*, 85.:5507–5511 (1988); herpes simplex virus, Smith, et al., *Proc. Natl. Acad. Sci. USA*, 83:2787–2791 (1986); and influenza virus, Zerial, et al., *Nuc. Acids. Res.*, 15:9909–9919 (1987).

The concept underlying this work is that an oligonucleotide complementary to a unique segment of a viral genome, or an RNA derived from it, may selectively disrupt processes dependent on that segment by hybridization. This rationale is supported by a variety of experiments with cell free systems or with cells to which "antisense" polynucleotides have been inserted by microinjection or transfection, C. A. & Cohen, J. S., *Cancer Res.*, 48:2659–2668 (1988). However, the actual mechanisms by which oligonucleotides and their analogs function as inhibitors in cell cultures are still far from clear. In particular, little is known about the interaction of the oligomers with cell membranes or the locus of their reactions within cells. It appears that non-ionic oligomers, such as the methyl phosphonate analogues diffuse passively through cell membranes.

S. E. Clare has synthesized oligonucleotides possessing one or more 2,2,2,-trichloral-1,1-dimethylethyl (TDCME, lipophilic) group of the phosphorous atom in the chain and show that this group on one strand with proper stereochemistry can inhibit cleavage of the opposite strand by a restriction endonuclease and that the same group on a template will inhibit synthesis of the complementary strand by the Klenow enzyme. S. E. Clare also demonstrated a single modification 5' to dGNAd (CG) octamer by TDCME group prevents the B to Z conformational transition. S. E. Clare, Ph.D. Dissertation, Northwestern University, Evanston, Ill. (1987).

The present invention is related to a family of oligonucleotides modified at the backbone so that the oligonucleotide may anchor at the cell membrane to provide antiviral effects. The present invention describes a family of oligonucleotides with a modification designed to anchor the oligomer, at least transiently at the cell membrane, to inhibit HIV-1 in cell culture. Fatty substances have been selected as an anchor for the oligonucleotide, and without being limitative, steroids such as cholesteryl have been selected as the preferred anchor since they are highly hydrophobic and cell membranes have an abundance of this steriod. The compounds may also have anti-sense activity.

The cholesteryl is a large lipophilic group, much larger than the TDCME group. In principle, such pendent groups, when linked covalently to the internucleotide phosphorous atoms, have potential as lipophilic centers to enhance the interaction with membranes, to alter partitioning of oligonucleotides within cells, to inhibit certain enzymatic reactions and to influence the stability of hybrids joined with natural polynucleotides. Cholesteryl is a component of any biological membrane and interacts with other lipids. The AIDS virus, HIV, is distinguished by an unusually high cholesteryl content in the lipid membrane. Early model studies by Finean, *Experientia*, 9:17–19 (1985), suggested that the cholesteryl molecule is capable of formation of a stabilizing complex with the phospholipid molecule. The hydrocarbon chain of the cholesteryl is bound to the parallel portion of the phospholipid chain by van der Woals forces. Recent studies employing a variety of techniques indicated that the major forces may involve the hydrophobic portion of the lipid molecules. Therefore, cholesteryl is a preferred modifying group for oligonucleotide interaction with cells.

SUMMARY OF THE INVENTION

The invention is concerned with oligonucleotides that are modified to anchor the oligomer at the cell membrane or eventually, intranuclearly, so that the oligonucleotide may serve as a probe.

More specifically, the invention provides a pharmaceutical composition including an oligonucleotide conjugated to asteroid for increasing the antiviral activity of the compound. One aspect of the present invention provides oligonucleotide compounds represented by the following structural formula:

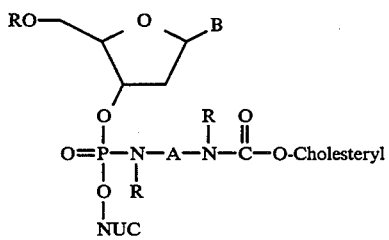

Formula I wherein A=aliphatic alkyl or branched aliphatic alkyl or a heteroatom containing an alkyl (branched) chain of 2 to 18 carbon atoms, preferably $CH_2$, R=H and lower alkyl up to 12 carbon atoms, preferably methyl; NUC refers to an oligonucleotide which may be a deoxyribonucleotide or a ribonucleosite. Preferred nucleotides are ethyladine, deoxyadenosine, deoxyguanosine and deoxycytidine. The nucleotides are connected respectively to the phosphorous through their 3' and 5' oxygens, B is a purine or pyrimidine base (such as Thy, Cyt, Gua, Ade).

Cholesteryl has been selected as the preferred anchol because it is highly hydrophilic and found in cell membranes. The cholesteryl modified oligonucleotides of the present invention have been found to inhibit HIV-1 in cell culture. The location of the insertion of the cholesteryl anchor on the oligonucleotide may be varied and is not dependent on sequence. However, other steriods are efficacious

DETAILED DESCRIPTION OF THE INVENTION

The novel compounds of Formula I can be prepared by convenient procedures for introducing a cholesteryl group at any desired internucleoside phosphorous in the course of synthesizing an oligonucleotide. The cholesteryl may be linked to an oligonucleotide as a substituent at either the 3'-O or 5'-O terminus.

Processes for preparing the novel compounds of Formula I are generally described by equations A and B.

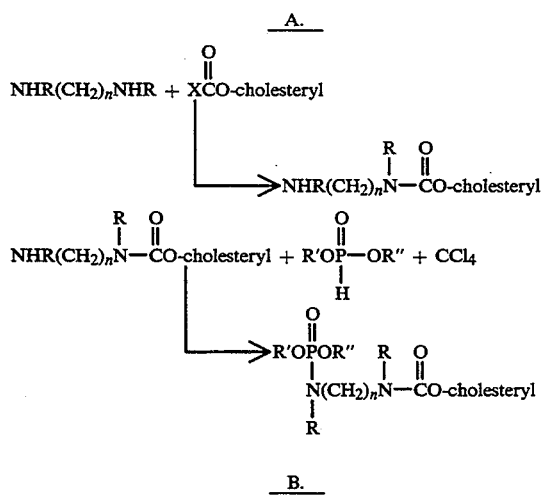

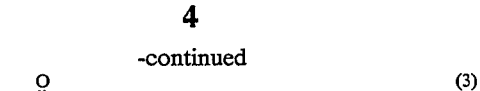

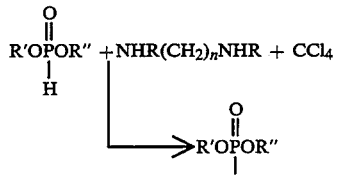

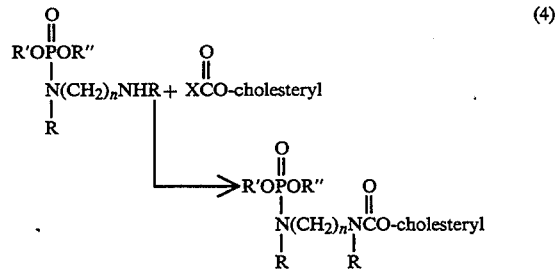

In the reactions, X=Cl— and p-nitrophenoxy, n=2 and 6, and R=H and methyl. The reactions for linking the amines to phosphorous are based on the general procedure of Froehler, B. C., *Tet. Lett.*, 27:5575–5578 (1986) for generating P—N bonds in oligonucleotide derivatives. The article is incorporated by reference.

Equation A avoids side reactions involving condensation at both nitrogen atoms of the diamine to form bisphosphoramidates. Procedures for preparing fifteen compounds of Table I with the cholesteryl anchor are described as follows: phosphodiester links were formed by cyanoethyl phosphoramidite chemistry described in the standard synthesis protocol provided by the manufacturer of the synthesizer, for example, Biosearch 8600, Biosearch, Inc., San Raphael, Calif. Chain extension by hydrogen phosphonate chemistry is described by Froehler, et al., *Tet. Lett.*, 27:469–472 (1986) and Froehler, et al., *Nuc. Acids. Res.*, 14:5399–5407 (1986). Phosphorothioate functional groups are added by the procedure of Froehler, et al., *Tet. Lett.*, 27:5575–5578 (1986).

Experimental Procedure 2-(Cholesteryloxycarbonylamino)ethylamine.

Cholesteryl chloroformate (2g) in dichloromethane (6 ml) was added dropwise to a solution of ethylenediamine (2.5 ml) in dichloromethane (6 ml) and pyridine (6 ml). The mixture was stirred for two hours; then the solvent was removed under vacuum and the residue was partitioned between water (150 ml) and dichloromethane (150 ml). The organic layer was washed with water, dried ($Na_2SO_4$), and concentrated to give the title compound; 1.6 g (76%), mp 149–155 degrees Centigrade. Recrystallization from cyclohexane afforded crystales melting at 152–155 degrees Centigrade; Rf on silica ($CHCl_3$/MeOH, 1/1 v/v) 0.15; positive ninhydrin test. Anal. Calcd for $C_{30}H_{52}N_2O_2$; C, 76.22; H, 11.09; N, 5.93. Found: c, 75.96; H, 11.10; N, 5.86.

Preparation of Cholesteryl-Modified Dinucleoside Monophosphate on CPG Support.

Internucleoside cholesteryl side chains were linked to phosphorous via phosphoramidate bonds (adaption of procedure of Froehler). The preparation of d-DMT-ibG$_c$ibG-CPG. is representative. A sample of DMT-ibG linked through the 3'-O to a controlled-porglass support (Biosearch) (250 mg. 8 micro moles of DMG-ibG) was placed in a Glencoe Gastight syringe (10 ml) equipped with a plug of glass wool at the inlet. Reactions and washings were carried out by drawing in and ejecting the desired solutions. Thus, the DMT groups were removed with dichloroacetic acid (2.5% in $CH_2Cl_2$; the support was washed repeatedly with $C_5H_5/CH_3CN$ (½), coupling was effected by drawing in together DMT-ibG-hydrogen phosphonate (80 mg., 0.1 mmol, in 1.2 ml $CH_3CN/C_5H_5$) and trimethylacetyl chloride (65 micro L, 0.5 micro moles, in 1.2 ml $CH_3CN/C_5H_5$, 1/1 v/v; 2 minutes), and the support was washed well with $CH_3CN/C_5H_5$. A solution of cholesteryloxycarbonylaminoethylamine (250 mg, 0.5 mmol) in $CCl_4$ (5 ml) and $C_5H_5$ (2 ml) was then drawn into the syringe and after 0.5 hours, the solution was ejected and the solid was washed well with $CH_3CN$. Appropriate portions were then transferred to a cartridge for extension by machine synthesis (Biosearch 8600 Synthesizer) or to a syringe for manual synthesis.

Chain Extension. The oligonucleotide chains were extended by conventional phosphoramidite chemistry in constructing phosphodiester links and by hydrogen phosphonate chemistry in building the phosphorothioate derivatives. The manual procedure used in adding a thymidine unit to DMT-ibG*G-CPG in synthesizing compound 2 in Table 1 is representative of one synthetic cycle utilizing a phosphoramidite reagent.

The DMT(G*G) loaded CPG (30 mg, 1 micro mole) was poured into a 1.0 ml Glenco Gas tight syringe with a glass wool plug at the inlet. Washes were effected by drawing up the desired amount of the reagent, resuspending the support by brief hand agitation, and ejecting the solution. The DMT protecting group was removed by washing with $DCA/CH_2Cl_2$ (2.5/100 v/v, 5.0 ml), and organ effluents were pooled from subsequent spectroscopy (447 nm) and calculation of the coupling efficiency. The support was washed successively with $C_5H_5N/CH_3CN$ (½, v/v, 1×0.5 ml), and $CH_3CN$ (2×0.5 ml). Any unreacted 5'-OH groups were capped by drawing DMAP in $C_5H_5N/THF$ (0.3M, 1/15, v.v, 0.5 ml) into the syringe followed immediately by $Ac_2O/THF$ (0.6M, 0.5 ml). The mixture was agitated for one minute, capping agents were ejected from the syringe, and the support was washed with $C_5H_5N/CH_3CN$ (½, v/v, 1×5.0 ml) and $CH_3CN$ (1×0.5 ml). The phosphite internucleoside linkage was oxidized to the phosphotriester linkage with $I_2$ in $C_5H_5N/THF H_2O$ (0.1M $I_2$, 18/80/2, v/v/v, 0.5 ml) for two minutes. The oxidant was ejected, and the support was washed with $C_5H_5N/CH_3CN$ (½, v/v, 3×1.5 ml) and $CH_3CN$ (3×1.5 ml) to complete one synthetic cycle.

For chain extension by hydrogen phosphonate chemistry the DMT-ibG*ibG-cpg (1 micro mole loaded dimer) was detrytylate as in the previous case. A solution of the DMT-nucleoside hydrogen phosphonate (10 mg, about 15 micro moles, in $CH_3CN/C_5H_5N$ (1/1, v/v, 0.3 ml) was drawn into the syringe, which was agitated for two minutes. The coupling agents were ejected from the syringe, and the support washed with $C_5H_5N/CH_3CN$ (1/1, v/v, 0.5 ml), and $CH_3CN$ (3×0.5 ml) to complete one synthetic cycle. Additional couplings were performed by returning to the initial wash and repeating the cycle. Oxidation following the final coupling step was performed by treatment with 0.1M sulfur in $CCl_4/Et_3N$ (9/1, v/v) at room temperature (two hours reaction). Procedures for machine syntheses were similar.

Isolation of Oligonucleotides

The oligomers were removed from the syringe or the synthesizer and warmed in a capped vessel with concentrated $NH_4OH$ at 55 degrees Centigrade for five hours. The aqueous solution was then removed and concentrated under reduced pressure to give the crude oligonucleotide. This substance was chromatographed on a C-18 column and the band corresponding to the desired target oligomer was collected and lyophilized.

TABLE 1

| | Properties of Oligonucleotides | | | | |
|---|---|---|---|---|---|
| compound | | HPLC$^a$ min | TLC$^b$ $R_f$ | PAGE$^c$ $R_m$ | $T_m^d$ °C. |
| 1 | ACACCCAATTCTGAAAATGG | 12.2 | 0.26 | 0.64 | 60 |
| | Cholesteryl Substituents | | | | |
| 2 | ACACCCAATTCTGAAAATG*G | 46.0 | 0.41 | 0.55 | 60 |
| 3 | AC<u>T</u>CC<u>G</u>AAA<u>G</u>ATAAAG*G | 46.6 | 0.43 | 0.54 | — |
| 4 | A*CACCCAATTCTGAAAATG*G | 61.0 | 0.58 | e | 52 |
| 5 | CAATTCTCAAAATG*G | 46.5 | 0.54 | 0.64 | 46.5 |
| 6 | $A_sC_sA_sC_sC_sC_sA_sA_sT_sT_sC_sT_sG_sA_sA_sA_sA_sT_sG_sG$ | 16.5 | 0.59 | 0.67 | 44 |
| 7 | $A_sC_sA_sC_sC_sC_sA_sA_sT_sT_sC_sT_sG_sA_sA_sA_sA_sT_sG*G$ | 40.2 | 0.61 | 0.64 | 47.5 |
| 8 | $C_sA_sA_sT_sT_sC_sT_sG_sA_sA_sA_sA_sT_sG_sG$ | 17.3 | 0.47 | 0.67 | 29 |
| 9 | $C_sA_sA_sT_sT_sC_sT_sG_sA_sA_sA_sA_sT_sG*G$ | 47.4 | 0.59 | 0.63 | 25 |
| 10 | $C_sT_sG_sA_sA_sA_sA_sT_sG*G$ | 15.6 | 0.52 | 0.76 | — |
| 11 | $C_sT_sG_sA_sA_sA_sA_sT_sG*G$ | 49.6 | 0.56 | 0.62 | — |
| 12 | $G_sA_sC_sT_sT_sT_sT_sA_sG*G$ | 45 | 0.60 | 0.79 | — |
| 13 | $C_sT_sG_sA_sT_sT_sT_sT_sG*G$ | 45.2 | 0.59 | 0.76 | — |
| 14 | $A_sA_sA_sG*G$ | 47.5 | 0.66 | 0.62 | — |
| 15 | $T_sT_sT_sT_sT_sT_sT_sT_sT_sT_sT_sT_sT_sT*T$ | 50.0 | 0.60 | 0.65 | 16 |

In formulas * represents $O=P-NH(CH_2)_2NHCO_2$ Cholesteryl; s represents $O=P-S^-$, and + represents $O=PNH(CH_2)_3N(CH_3)_2$. Altered nucleotides in 7 are underlined.

$^a$Elution time, Hewlett-Packard RP-C18 column (10 cm); 0.1M triethylammonium acetate (pH 7.0), 1%/min acetonitrile gradient starting at 0% acetonitrile; 0.5 ml/min flow rate.

$^b$Thin layer chromatography on Merck silica plates with propanol/ammonium hydroxide/water, 55/10/35 v/v/v.

$^c$Polyacrylamide gel electrophoresis in 20% cross-linked gel at pH 8.0, $R_m$ is migration relative to bromophenol blue.

$^d T_m$ is the temperature at the midpoint for the maximum slope in a plot of $A_{260}$ versus temperature in 0.1M aqueous NaCl, 0.01M Tris buffer at pH 7.0; total nucleotide concentration (base units) in approximately $10^{-4}$M. In each case, the complement is a phosphodiester strand equal in length to the modified oligomer.

*The sample appeared as a broad streak starting at $R_m$ 0.2. The complement for determination of $T_m$ was poly d(A).

Coupling efficiency introducing a cholesteryl fragment to the compounds of Table 1 exceeded 50%.

As noted, phosphodiester links were formed in compounds 2-5 by conventional cyanoethyl phosphoramidaite chemistry as described in the standard synthesis protocol provided by the manufacturer of the synthesizer, Biosearch, Inc., San Raphael, Calif. For compounds 6-15, the chains were extended by hydrogen phosphonate chemistry as described by Froehelr, et al., Tet. Lett., 27:469-472 (1986) and Froehler, et al., Nuc. Acids. Res., 14:5399-5407 (1986) the final oxidation with sulfur to generate the phosphorothioate groups.

The compounds were characterized by HPLC, TLC, PAGE, thermal disassociation curves for hybrids formed with complimentary strands and by UV and NMR spectroscopy. The NMR spectra exhibited the characteristic peaks for phosphodiester, phosphoramidate and phosphorothioate functional groups. A proton NMR spectrum of compound 2 shows the presence of the cholesteryl fragment. Further, the hydrophobic nature of the cholesteryl-oligonucleotides was shown by the HPLC data in Table 1. For example, the elution times for samples analyzed by a reverse phase C-18 column increased from 14 to 46 to 61 minutes for the series 1 (control), 2(one) cholesteryl, and 4(two) cholesteryl, respectively. Susceptibility, to nuclease degradation was examined with compound 2. In the presence of snake venom, phosphodiesterase, an alkaline phosphatase, compound 2 was completely hydrolyzed to the expected nucleosides and the fragment corresponding to the terminal G*G.

The data in Table 1 shows that the introduction of a single cholesteryl fragment at a terminal internucleoside position has only a minor effect on the stability of the hybrid duplex as measured by $T_m$ values when compound 1 is compared with 2; compound 6 compared with 7, and compound 8 compared with 9. Conversely, two cholesteryl substitutents led to appreciable destabilization for the 20-mer compound, compare compound 4 with 1. The disassociation of complexes formed from equi-molar quantities in modified and unmodified complementary oligodeoxyribo-nucleotides were measured by changes in adsorbents in 260 nm as a function of temperature.

Additional compounds were made in accordance with Equation B, wherein $R=CH_3$, $N=6$, $X=-OC_6H_5MO_2$. The following compounds were prepared: 16, TTTTTTTTT#T; 17, T#TTTTTTTT; 18, TTTT#TTTTTT; and 19, CGCG#AATTCGCG, where # is $O=P-N$ $(CH_3)(CH_2)CO_2$ cholesteryl. The procedures of Froehler, B. C., Tet. Lett., 27:5575-5578 (1986) and Marcus=Sekura, et al., Nuc. Acids. Res., 15:5749-5763 (1987) were followed in preparing phosphodiester links in compounds with internal modifications to avoid or minimize complications which could arise from the premature formation of phosphodiester groups in the course of the synthesis. As in the case of the derivatives of ethylenediamine, introduction of substituents at the terminal internucleoside links had little effect on $T_m$ values for the hybrids formed in complementary sequence ($T_m$ for 1:1 complexes with poly d(A) in 0.1M NaCl, pH 7: 28 degrees Centigrade for compound 16, 27 degrees Centigrade for compound 17 and 28 degrees Centigrade for parent $T_9T$). Conversely, modification of the centrally positioned internal link led to significant destabilization (21 degrees centigrade $T_m$ for compound 18). The mobility of stereoisomers of compound 19 on HPCL differed sufficiently to permit separation of the isomers. The $T_m$ for the duplexes formed from these self-complementary modified strands (stereoisomers of compound 15) were substantially lower than that for the parent duplex ($T_m$: 40 degrees and 45 degrees Centigrade for the isomers as compared to 56 degrees Centigrade for CGCGAATTCGCG; 0.1M NaCl, pH 7.0).

The linking of cholesteryl to an oligonucleotide as a substituent at the 5'-O terminus is quite simple and can be shown by the following example.

Synthesis and characterization of cholesteryl-sTsGsG.

DMT(G) loaded CPG (88.2 mg, about 3 micro moles) was poured into 5 ml Glencoe gas tight syringe with a glass wool plug at the inlet. Washes were effected by drawing up the desired amount of the reagent, resuspending the support by brief hand agitation and ejecting the solution. The support was initially washed with $CH_3CN$ (4.5 ml×3) and $CH_2Cl_2$ (4.5 ml×2). The DMT protecting group was removed by washing with $DCA/CH_2Cl_2$ (2.5/100, v/v, 10 ml). All of the orange effluents were pooled for subsequent spectroscopy (448 nm) and calculation of the coupling efficiency.

The support was washed successively with pyridine/$CH_3CH$ (¼, v/v, 4.5 ml×3), $CH_3CN$ (4.5 ml×4) and dry $CH_3CN$ (4.5 ml×6). The H-phosphonate solution (for G and T-36 mg, about 0.06 micro moles in dry $CH_3CH$/pyridine, 1/1, v/v, 2ml); for cholesteryl H-phosphonate-42 mg., about 0.09 micro moles in dry $CH_3CN$/pyridine, ⅓, v/v, 2.0 ml) and trimethylacetyl chloride solution (0.03 ml, about 0.351 micro moles in trimethylactyl chloride solution (0.03 ml, about 0.351 micro moles in dry $CH_3CN$/pyridine, v/v, 2 ml) were drawn into the syringe, which was agitated for five minutes (but for 15 minutes for cholesteryl H-phosphonate coupling). After each coupling, the reagents were ejected from the syringe and the procedure was continued by returning to the initial wash steps.

Oxidation, following final coupling step and wash with dry $CH_3CN$ (4.5 ml×3), dry pyridine (4.5 ml×4) was performed with 0.1 58 in $CS_2$/pyridine (1/1, v/v, 4.5 ml×2), $CH_3N$ (4.5 ml×3), dry $CH_3CN$ (4 ml×3) and ether (5 ml×4). After drying the CPG-bound product was treated with 3.0 ml concentrated $NH_4OH$ at 55 degrees Centigrade for five hours. Upon removal of $NH_4OH$ by evaporation under reduced pressure, CPG support was removed by filtration; the filtrate freeze-dried overnight and the product redissolved in 2.0 ml $H_2O$. For UV spectroscopy, 10 micro liters of this solution were added to 990 micro liters of $H_2O$.

HPLC data indicated about 50% of the reaction mixture was the desired product. Spectroscopic methods also confirm the desired structure.

Compound of Formula I of the present invention can also be utilized in a method for hybridizing with a complementary sequence in a solution under conditions conducive to the hybridization. Typically, these conditions are controlled by the complementary sequence. The specific conditions needed for hybridization would be known to one skilled in the art familiar with the complementary sequence and environment for hybridization.

The present invention further comprises the method of modifying the backbone of an oligonucleotide by the attachment of a fatty substance, preferably cholesteryl so that it will anchor into the cell membrane so that the modified oligonucleotide will hybridize with the complementary sequence. By anchoring into the cell membrane, the oligonucleotide may provide diagnostic or therapeutic activity. For example, the oligonucleotide compound 1 of Table 1 is complementary to the splice acceptor for site at 5349-5368 in HIV-1 and has been shown to inhibit replication of this virus in MOLT-3 cells by Zerial, et al., *Nuc. Acids Res.*, 15:9909-9919 (1987) and Stein, et al., *Cancer Res*, 48:2659-2668 (1988). The compounds shown in table 1 are structural variations of the basic sequence of compound 1. Compounds 2-15 were designed to provide information on the antiviral properties of the cholesteryl modified oligonucleotides and, specifically, on the dependence of the antiviral activity on 1 (the number of cholesteryl fragments incorporated in the backbone chain), 2 (the nature of the main backbone section e.g. phosphodiester venus phosphorothioate links), 3 (the length of the oligonucleotide) and 4 (the sequence integrity of the oligonucleotide.

Samples of the oligomers were assayed in the following test:

Assays for HIV-1 Inhibition.

The inhibition of HIV-1 expression of H9 or MOLT-3 cells in the presence of antisense oligonucleotides was carried out by infecting $5 \times 10^5$ cells per ml with $2.5-5 \times 10^8$ virus particles of HIV-1 strains HTLV-IIIB or HTLV-IIIC. Infection with 500-1000 virus particles per cell represents a multiplicity of infection (MOI) of 0.5-1. HIV-1 infection of cells was carried out by simultaneous addition of virus and cholesteryl modified oligomers to the cells in culture. The cultures were incubated in culture medium containing RPMI 1640, 10% (v/v) fetal bovine serum, 2 mM gultamine, and 250 micrograms of gentamicin per ml, in a humidified atmosphere containing 5% $CO_2$ at 37 degrees Centigrade. After four days, the cells and supernatant were examined for the level of HIV-1 expression by measuring syncytia (MOLT-3 cells) and viral antigen expression as well as cell viability. The number of syncytia formed MOLT-3 cells were counted after triturating the cells to obtain an even distribution of the syncytia in the culture. The average number of syncytia as obtained by counting several fields in duplicate cultures. Cell viability was measured in the presence of trypan blue, and the cells that excluded the dye were counted as viable cells. HIV-1 antigen expression was measured in cells fixed in methanol/acetone as described. Satin, et al., *Biochem. Pharmacol.*, 34:075-4078 (1985) and Sarin, et al., *J. Natl. Cancer Inst.*, 78:663-666 (1987). In brief, the cells were pelleted and then resuspended in phosphate-buffered saline (PBS) at a concentration of $10^6$ cells per ml. The cells were spotted on toxoplasmosis slides, air-dried, and fixed in methanol/acetone (1:1, v/v) for 15 minutes at room temperature. The slides were next incubated with 10% normal goat serum at room temperature for 30 minutes and washed with PBS four times. HIV-1 p24 or P17 monoclonal antibody was added to each well and the slides were incubated for 30 minutes in a humid chamber 15 37 degrees Centigrade. The slides were then washed four times with PBS, incubated with fluorescein isothiocyanate-labeled goat anti-mouse IgG (Cappel Laboratories, Cochranville, Pa.) for 30 minutes at 37 degrees Centigrade, and then washed with PBS overnight. The slides were counterstained with Evan's blue, washed with PBS, mounted with 50% glycerol, and examined with a Zeiss fluorescence microscope. The percentages of cells fluorescing in the oligomer-treated and untreated cultures were compared. Inhibition of HIV-1 expression in the presence of oligomers was found to be similar in both the $H_9$ and the MOLT-3 cells.

Inhibition of HIV-1 expression and H9 and MOLT-3 cells in the presence of cholesteryl modified oligonucleotides was carried out and results shown in Tables 2 and 3.

The data for the inhibition of formation of syncytia, an expression of HIV proteins P17, P24 and reverse transcriptase shown for compounds 1-5 in Table 2 and compounds 6-16 in Table 3. The tables show results in $ID_{50}$ values for inhibition of syncytia (concentration of an oligomer in micro grams/mi. It gives 50% inhibition under the assay condition) as an index.

The data from the tables describe favorable conclusions. The activity of the parent oligonucleotide, compound 1, is relatively low (ID50 less than 100). It appears that anchoring a cholesteryl fragment to the oligonucleotide significantly enhances the anti-HIV activity (from ID50 greater than 100 to 10). Thus, the cholesteryl provides steroid means conjugated to the oligonucleotide for increasing the antiviral activity of the oligonucleotide. Further, anchoring a second cholesteryl fragment does not appear to be an improvement because the second cholesteryl leads to a reduction in activity relative to the monocholesteryl-oligonucleotide. It appears that a cholesteryl fragment to a phosphorothioate oligonucleotide analog enhances the antiviral property of the phosphorothioate derivative as shown in comparisons between compounds 6 and 7, 8 and 8, and 10 and 11. In the most favorable case, compound 7, the ID50 was reduced to 0.8 micrograms per milliter. With relatively large oligomers, those having 15 to 20-mers, the activity of the cholesteryl-oligonucleotides (natural phosphodiester links) appears to be independent of the chain link (compare compounds 2 and 5). A lack of dependence of activity on link has also been shown for unmodified oligonucleotides in the 15-20 mer range. Additionally, the activity of the cholesteryl modified phosphorothioate derivates shows a downward trend as the length of the oligomer is decreased. Thus, The ID50 values increase from 0.8 for the 20-mer (compound 7) to about 3.5 for the 10-15 mers (compound 11 and 9), to 13 for the 6-mer (compound 14).

From Tables 2 and 3, it can also be concluded that the anti-HIV activity of the cholesteryl-modified oligonucleotides is not strongly dependent on the nucleotide sequence. This conclusion applies both to the phosphodiester and the phosphorothioate cholesteryl derivatives (compared to the data for compounds 2 and 3 has six mismatched base sites; and the data for compound 11 with that for compounds 12 and 13 which have 8 and 3 mismatched). For phosphorothioate derivatives, the activity of all three 10-mers is essentially the same although the sequence is different. Further, the cholesteryl modified oligomers are not toxic to cells even at concentrations far in excess of those that lead to complete inhibition of the replication of HIV. For all derivates the LB50 was greater than 100 micrograms per ml.

Additional Oligonucleotides having Steroids Conjugated Thereto Possessing Antiviral Activity Additional compounds and their antiviral activity are set forth in Table 4. Activity is reported as the average ID50 values (the concentration in micrograms per ug/ml of oligomer that leads to 50% inhibition of virus) determined by syncytia formation and expression of the viral proteins P17 and P24. The procedure is referenced in Letsinger et al (1989) *Proc. Natl. Acad. Sci. USA*, 86:6553–6556. The abbreviations used in the Table are set forth below.

... NsN' ... internucleoside phosphorothioate link, as in ... CsG ...

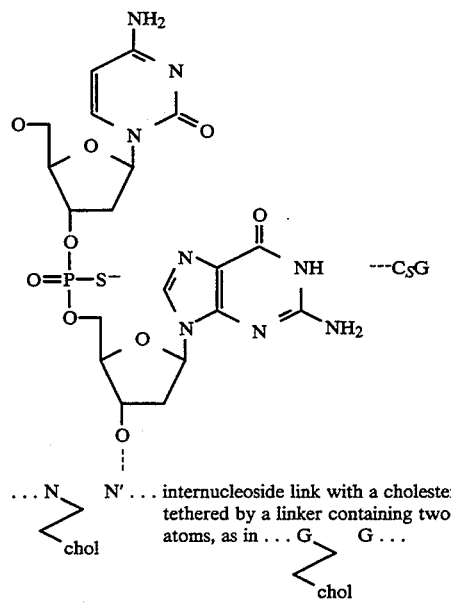

... N⟩chol   N' ... internucleoside link with a cholesteryl group tethered by a linker containing two carbon atoms, as in ... G⟩   G ...
                                                                                          chol

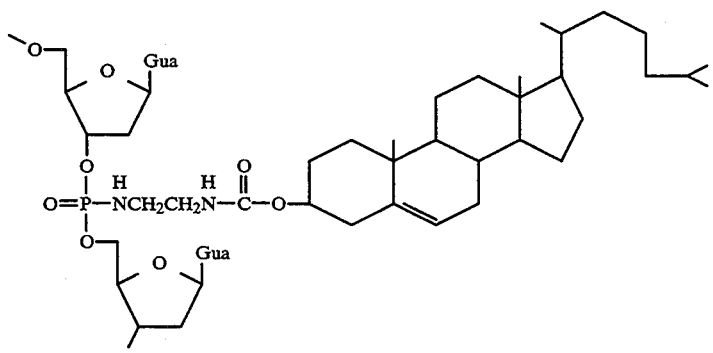

... N⟩chol   N' ... internucleoside link with a cholesteryl group tethered by a linker containing ten carbon atoms, as in ... G⟩   G ...
                                                                                          chol

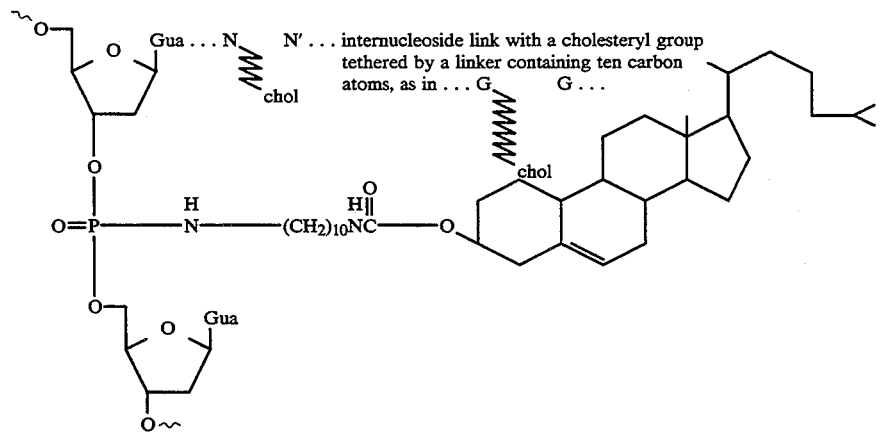

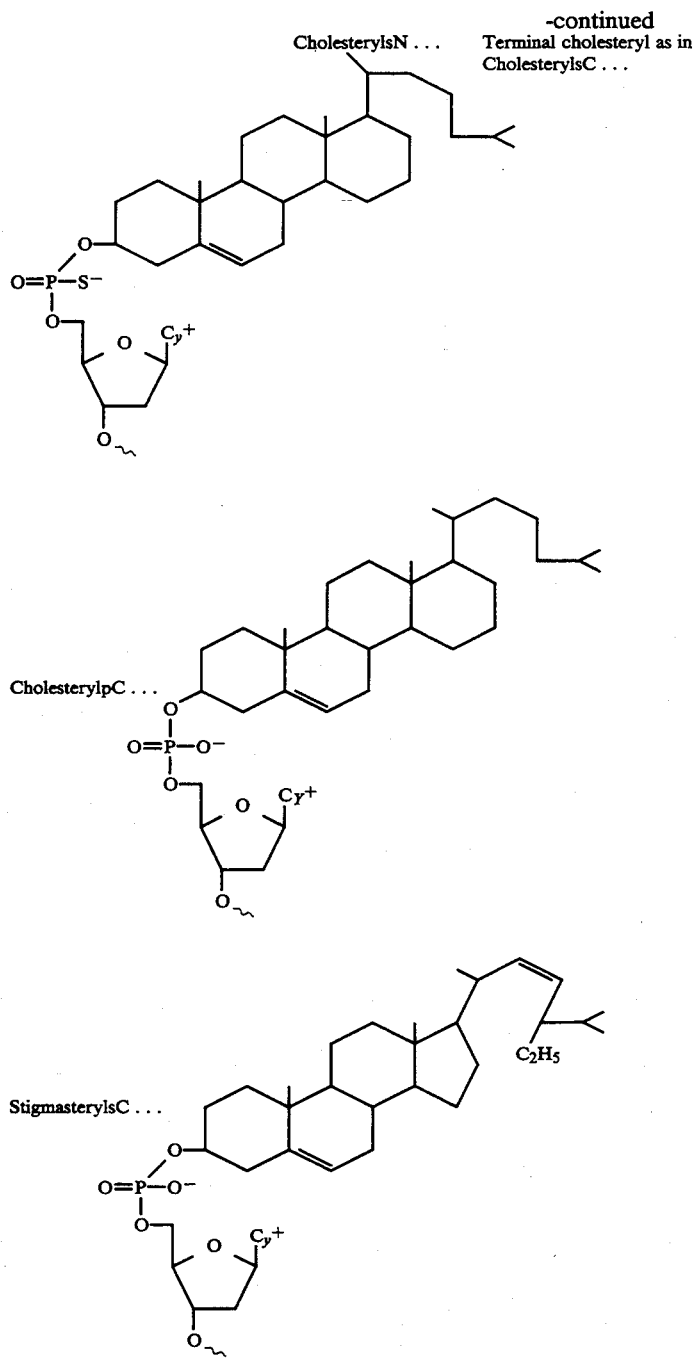

EXPERIMENTATION

All compounds were synthesized on controlled pore glass supports using a Biosearch 8600 DNA synthesizer or a syringe for manual manipulation. Internucleoside phosphorothioate links in compounds 1–4, 6, 8–16 were generated by conventional hydrogen phosphonate chemistry using 5'-dimethoxytritylnucleosides and terminal oxidation of all hydrogen phosphonate links with sulfur. Cholesteryl was joined to the chain in 1–4, 8, 10, 12, 14–16 by oxidative coupling of 2-(cholesteryloxycarbonylamino)-ethylamine at an internucleoside hydrogen phosphonate link via reaction with carbon tetrachloride. The procedure for tethering cholesteryl in compounds 11 and 13 was identical except that 2-(cholesteryl-oxycarbonylamino)-decylamine was used as the amine component. All these procedures are described in the original patent application and/or reference 1. For synthesis of 6, cholesteryl was joined utilizing cholesteryl H-phosphonate. For the synthesis of compounds with phosphodiester links 5' to phosphorothioate links (compounds 5 and 7), chains were built using methyl phosphoramidate coupling followed by oxidation with sulfur at each step. W. J. Stec, et al, *Am. Chem. Soc.*, 106:6077 (1984). The terminal cholesteryl phosphate was added by oxidative coupling with cholesteryl H-phosphonate and carbon tetrachloride, as for compound 6, followed by standard oxidation with iodine/water. Treatment with thiophenol to remove the methyl protecting groups and ammonium hydroxide to remove base protecting groups and cleave the oligomer from the solid support the afforded the modified oligonucleotide.

Compounds 15, 16 and a related substance, compound 17 with the structure XsXsXsXsXsXsXsXsX$_{chol}$T, were prepared using the syringe technique and DMT-OCH$_2$CH$_2$CH$_2$OP(O)(H)O$^-$ (compound 18 in place of a nucleoside H-phosphonate. For synthesis of 18, 1,3-propanediol (75 mmol) was stirred with dimethoxytrityl chloride (15 mmol) in dry pyridine (25 ml) for about 20 hours at room temperature. Addition of water (100 ml), extraction with chloroform, and chromatography on a silica gel column afforded 3-dimethoxyltrityloxypropanol as a viscous oil; 56% yield; NMR in CDCl$_3$: 1.85 (p, 2H, —CH$_2$—), 2.21 (broad t, 1H, O—OH), 3.28 (broad t, 2H, —CH2(OH), 3.79 (broad t, 8H, two CH$_3$O—), 6.82 (q, 4H), 7.21–7.42 (m, 9H aromatic). This alcohol (6.9 mmol), in dry acetonitrile (100 ml) was added dropwise over a period of 1 hour to phosphitilating solution prepared from phosphorus trichloride (30 mmol), imidazol (98 mmol), and triethylamine (104 mmol) in acetonitrile (100 ml) at ice-bath temperature. After one hour of stirring the flask was allowed to warm to room temperature and to stand for two hours. Water (50 ml) was added and the mixture was concentrated under reduced pressure and extracted with chloroform. Chromatography on silica gel afforded 20.0 g (62%) of 18 as the triethylammonium salt; mp 132°–135° C.; (CDCl$_3$): ppm 1.22 (t, 9H), 1.91 (p, 2H), 2.93 (q, 6H), 3.13 (t, 2H), 3.72 (S, 6H), 3.97 (t, 2H), 6.05 and 7.57 (singlets each, 1H), 6.77 (q, 4H), 7.14–7.39 (m, 9H).

Referring to Table 4, compound 1 is complimentary to a region in HIV-I coating for a splice site for the TAT gene compound 3 is complimentary to a region for REV gene. Compound 4 is complimentary to a region for NEF gene.

Compounds 2, 5, 6, 7, 8 and 9 are all based on sequence 1, with variations in position, mode of attachment, and the structure of the lipophilic steriod conjugate.

Compounds 10–14 are conjugates of homopolymers of nucleotides.

Referring to the activites shown in Table 4, compounds 1, 3, and 4, which are complimentary to various regions of the HIV-I virus, all show unusually high antiviral activity. These compounds may function by an antisense mechanism. Compound 3 is the most active cholesteryl-conjugated oligonucleotide that has been investigated.

Oligonucleotide phosphorothioate derivatives bearing two cholesteryl groups, one tethered at an internal position, are active, as demonstrated by compounds 2 and 14. Activity for an oligonucleotide with cholesteryl groups tethered at the 5' and 3' terminal internucleoside positions as set forth above it has been reported.

Cholesteryl conjugates with mixed phosphorothioate and phosphodiester backbones are active as demonstrated by compounds 2, 5, and 7. As shown by compounds 5, 6, and 7, oligomers with cholesteryl attached at the 5' end, either by a phosphodiester or a phosphorothioate link, are active. The activity is not strongly dependent on which of these links is used; that is, ID50 is 7 ug/ml for the phosphorothioate, compound 6, while is it 12 ug/ml for the phosphodiester, compound 7.

Linkage by the carbonylaminoethylamidate, such as in compound 8, affords a more active compound than linking by a phosphodiester, such as compound 7, or a phosphorothioate, such as compound 6.

Other highly lipophilic groups, such as stigmasteryl (compound 9) are comparable to cholesteryl in enhancing the antiviral activity of the oligonucleotide derivatives.

Cholesteryl conjugated homooligomers containing thymidine, such as compounds 10, and 11, or deoxycytidine, such as compounds 12, and 13, are active antiviral pharmaceutical compositions. The deoxycytidine oligomers are somewhat active than the thymidine derivatives.

Tethers between the steriod and the oligonucleotide having long carbon chains of for example 10 methylene groups, as well as short carbon chains of 2 methylene groups can be used in linking the cholesteryl to the phosphorus atom, as shown by comparing data for the thymidine derivatives (compounds 10 and 11) and the deoxycytidine derivatives (compounds 12 and 13. The compounds with the linker —NH(CH$_2$)$_{10}$NHCO— exhibit about the same activity as the corresponding compounds with the linker —NH(CH$_2$)$_2$NHCO—.

In view of the above, applicant has demonstrated the antiviral activity of the pharmaceutical composition of an oligonucleotide conjugated to a steriod. Applicant has shown that the oligonucleotide can be a homooligomer as well as a specific nucleotide sequence complimentary to various regions of a virus, such as the HIV-I virus. Applicant has also shown that various steriods conjugated to the oligomer have antiviral activity.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

TABLE 2

Inhibition of HIV by Oligonucleotides with Cholesteryl Substituents

| compound | conc. µg/ml | % inhibition syncytia | P24 | RT | ID$_{50}$ µg/ml (syncytia) |
|---|---|---|---|---|---|
| 1 (control) | 0.16 | 0 | | | >100 |
| | 0.8 | 3 | | | |
| | 4 | 20 | | | |
| | 20 | 34 | | | |
| | 100 | 45 | | | |
| 2 | 2 | 0 | 0 | | 10 |
| | 5 | 4 | 0 | 0 | |
| | 10 | 51 | 63 | 48 | |
| | 20 | 95 | 88 | 90 | |
| | 50 | 100 | 100 | 92 | |
| 3 | 2 | 0 | 0 | 0 | 16 |
| | 5 | 2 | 13 | 0 | |
| | 10 | 22 | 70 | 0 | |
| | 20 | 77 | 69 | 0 | |
| | 50 | 100 | 100 | 84 | |
| | 100 | 100 | 100 | 100 | |
| 4 | 2 | 0 | 0 | 0 | 32 |
| | 5 | 3 | 0 | 0 | |
| | 10 | 7 | 0 | 0 | |
| | 20 | 28 | 32 | 26 | |
| | 50 | 85 | 88 | 75 | |
| | 100 | 100 | 100 | 100 | |
| 5 | 2 | 0 | 0 | 0 | 11 |
| | 5 | 5 | 0 | 0 | |
| | 20 | 92 | 100 | 82 | |
| | 50 | 100 | 100 | 100 | |
| | 100 | 100 | 100 | 100 | |

TABLE 3

Inhibition of HIV by Phosphorochioate Oligonucleodides with Cholesteryl Substituents

| compound | conc. µg/ml | % inhibition syncytia | P17 | P24 | RT | ID$_{50}$ (syncytia) |
|---|---|---|---|---|---|---|
| 6 (phosphodiester control) | 2.5 | 15 | 18 | 22 | 33 | 6.0 |
| | 6.25 | 56 | 67 | 81 | 70 | |
| | 10 | 90 | 89 | 89 | 85 | |
| | 25 | 100 | 100 | 100 | 100 | |
| 7 | 0.25 | 0 | 12 | 19 | 23 | 0.8 |
| | 1.0 | 74 | 69 | 70 | 68 | |
| | 1.5 | 100 | 100 | 100 | 100 | |
| | 6.0 | 100 | 100 | 100 | 100 | |
| 8 (phosphodiester control) | 1.6 | 0 | 0 | 0 | 0 | 14.5 |
| | 6.25 | 15 | 16 | 26 | 26 | |
| | 25 | 95 | 84 | 82 | 67 | |
| | 100 | 97 | 96 | 96 | 78 | |
| 9 | 1.6 | 28 | 39 | 43 | 47 | 3.2 |
| | 6.25 | 98 | 92 | 96 | 73 | |
| | 25 | 98 | 96 | 96 | 76 | |
| | 100 | 98 | 96 | 96 | 88 | |
| 10 (phosphodiester control) | 1.6 | 0 | 0 | 0 | 0 | >100 |
| | 6.25 | 0 | 4 | 4 | 0 | |
| | 25 | 0 | 20 | 22 | 25 | |
| | 100 | 0 | 24 | 33 | 28 | |
| 11 | 1.6 | 30 | 42 | 47 | 45 | 3.5 |
| | 6.25 | 97 | 86 | 88 | 61 | |
| | 25 | 97 | 92 | 92 | 70 | |
| | 100 | 98 | 92 | 96 | 89 | |
| 12 | 1.6 | 28 | 33 | 40 | | 3.4 |
| | 6.25 | 93 | 60 | 67 | | |
| | 25 | 100 | 100 | 100 | | |
| | 100 | 100 | 100 | 100 | | |
| 13 | 1.6 | 20 | 23 | 31 | | 3.6 |
| | 6.25 | 89 | 56 | 67 | | |
| | 25 | 100 | 100 | 100 | | |
| | 100 | 100 | 100 | 100 | | |
| 14 | 1.6 | 18 | 21 | 25 | | 1.3 |
| | 6.25 | 35 | 30 | 32 | | |
| | 25 | 90 | 70 | 66 | | |
| | 100 | 100 | 100 | 100 | | |
| 15 | 25 | 80 | 20 | 25 | | |
| | 50 | 99 | 99 | 90 | | |
| | 100 | 100 | 100 | 95 | | |

TABLE 4

New Modified Oligonucleotides

| Compound | Structure | ID50 (ug/ml)$^a$ |
|---|---|---|
| 1$^b$ | AsCsAsCsCsCsAsAsTsCsTsGsAsAsAsAsTsG>G<chol | 0.4–0.7 |
| 2 | AsCsAsCsCsCsAsAsTsCsTsGsAsAsAsA TpG>G with chol,chol | 1.7 |
| 3 | GsTsGsTsCsTsCsCsCsCsTsTsCsTsTsCsCsTsGsCsGA>T<chol | 0.05 |
| 4 | AsGsTsCsCsAsTsTsGsGsTsCsTsTsAsAsAsGsGsTsAsCsCsCsTsGsAsG>G<chol | 0.3 |
| 5 | CholesterylpAsCsAsCsCsCsAsAsTsTsCsTsGsAsAsAsAsTsGsG | 1.5 |
| 6 | CholesterylsCsTsGsAsAsAsAsTsGsG | 7 |
| 7 | CholesterylpCsTsGsAsAsAsAsTsGsG | 12 |
| 8 | CsTsGsAsAsAsAsTsG>G<chol | 1.5–2.5 |
| 9 | StigmasterylsCsTsTsGsAsAsAsAsTsGsG | 7–14 |
| 10 | TsTsTsTsTsTsTsTsT>T<chol | 10–18 |
| 11 | TsTsTsTsTsTsTsTsT>T with multiple chol | 15–30 |
| 12 | CsCsCsCsCsCsCsCsC>C<chol | 6 |

TABLE 4-continued

New Modified Oligonucleotides

| Compound | Structure | ID50 (ug/ml)[a] |
|---|---|---|
| 13 | CsCsCsCsCsCsCsC C <br> chol | 7 |
| 14 | CsCsCsCsCsCsC CsC C <br> chol chol | 1.7 (toxic > 4 ug/ml) |

[a] A range in activity is shown for compounds tested more than once.
[b] This compound, reported previously, is included for reference.

What is claimed is:

1. An oligonucleotide and a steroid conjugated to said oligonucleotide, said oligonucleotide comprising:

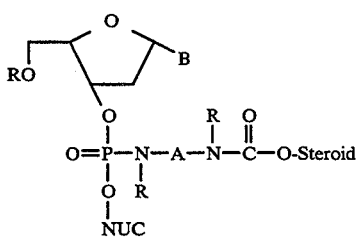

wherein A is selected from the group consisting of an aliphatic alkyl, branched aliphatic alkyl and an alkyl (branched) chain of 2 to 18 carbon atoms, R is selected from the group consisting of H and lower alkyl up to 12 carbon atoms; B is a naturally occurring base, the steroid is bound to said oligonucleotide utilizing the naturally occurring bases through an (-oxycarbonyl-amino)-decylamine-moiety, and NUC is an oligonucleotide.

2. An oligonucleotide as set forth in claim 1 wherein said steroid is cholesterol conjugated to said oligonucleotide.

3. A oligonucleotide as set forth in claim 2 wherein said oligonucleotide includes phosphodiester bonds.

4. A oligonucleotide as set forth in claim 3 including phosphorothioate substitutions of phosphodiester bonds.

5. An oligonucleotide as set forth in claim 1 wherein said steroid is stigmasteryl.

6. An oligonucleotide as set forth in claim 1 wherein the steroid is a (steroidyloxycarbonylamino)-decylamine.

* * * * *